United States Patent
Teles et al.

(10) Patent No.: US 7,803,971 B2
(45) Date of Patent: Sep. 28, 2010

(54) METHOD FOR THE PRODUCTION OF CYCLOPENTANONE

(75) Inventors: Joaquim Henrique Teles, Otterstadt (DE); Beatrice Rößler, Bad Dürkheim (DE); Thomas Genger, Lambsheim (DE); Andreas Glass, Lambsheim (DE)

(73) Assignee: BASF Akiengesellschaft (DE)

( * ) Notice: Subject to any disclaimer, the term of this patent is extended or adjusted under 35 U.S.C. 154(b) by 0 days.

(21) Appl. No.: 11/575,839

(22) PCT Filed: Sep. 23, 2005

(86) PCT No.: PCT/EP2005/010346

§ 371 (c)(1),
(2), (4) Date: Mar. 22, 2007

(87) PCT Pub. No.: WO2006/032532

PCT Pub. Date: Mar. 30, 2006

(65) Prior Publication Data

US 2008/0021247 A1    Jan. 24, 2008

(30) Foreign Application Priority Data

Sep. 23, 2004   (DE) .................. 10 2004 046 171

(51) Int. Cl.
C07C 45/27       (2006.01)
C07C 45/28       (2006.01)
(52) U.S. Cl. ...................... 568/363; 568/365
(58) Field of Classification Search .................. 568/365
See application file for complete search history.

(56) References Cited

U.S. PATENT DOCUMENTS

| 2,636,898 | A  | 4/1953  | Buckley |
| 3,656,899 | A  | 4/1972  | Baechle et al. |
| 4,177,645 | A  | 12/1979 | Schwarz |
| 5,849,257 | A  | 12/1998 | Fujiwara et al. |
| 7,105,704 | B2 | 9/2006  | Panov et al. |
| 2005/0203316 | A1 | 9/2005 | Panov et al. |
| 2006/0106258 | A1 | 5/2006 | Panov et al. |

FOREIGN PATENT DOCUMENTS

| DE | 2040219 | | 3/1971 |
| DE | 2732267 | A1 | 1/1979 |
| DE | 10319489 | A1 | 11/2004 |
| EP | 1076217 | A2 | 2/2001 |
| GB | 649680 | | 1/1951 |
| GB | 1327401 | | 8/1973 |
| JP | 2000053597 | | 2/2000 |
| WO | WO-98/25698 | | 6/1998 |
| WO | WO-00/73202 | | 12/2000 |
| WO | WO-03/078370 | A1 | 9/2003 |
| WO | WO-03/078371 | A1 | 9/2003 |
| WO | WO-03/078372 | A1 | 9/2003 |
| WO | WO-03/078374 | A1 | 9/2003 |
| WO | WO-03/078375 | A1 | 9/2003 |
| WO | WO-2004/000777 | A1 | 12/2003 |

OTHER PUBLICATIONS

Uriarte, Anthony. Nitrous Oxide (N2O)- Waste to Value. Studies in Surface Science and Catalysis, 2000, vol. 130, pp. 743-748.*
Bridson-Jones, F. S. et al., "Oxidation of Organic Compounds by Nitrous Oxide", J. Chem. Soc., 1951, pp. 2999-3008.
Dubkov, K. A. et al., "Non-Catalytic Liquid Phase Oxidation of Alkenes with Nitrous Oxide. 2. Oxidation of Cyclopentene to Cyclopentanone", React. Klnet. Catal. Lett., 2002, vol. 77, No. 1, pp. 197-205.
Panov, G. I. et al., "Non-Catalytic Liquid Phase Oxidation of Alkenes with Nitrous Oxide. 1. Oxidation of Cyclohexene to Cyclohexanone", React. Kinet Catal. Lett., 2002, vol. 76, No. 2, pp. 401-406.
Starokon, E. V. et al., "Liquid Phase Oxidation of Alkenes with Nitrous Oxide to Carbonyl Compounds", Adv. Synth. Catal., 2004, vol. 346, pp. 268-274.
Uriarte, A. K., "Nitrous Oxide (N$_2$O)—Waste to Value", Stud. Surf. Sci. Catal., 2000, vol. 130, pp. 743-748.

* cited by examiner

*Primary Examiner*—Sikarl A Witherspoon
(74) *Attorney, Agent, or Firm*—Connolly Bove Lodge & Hutz LLP

(57) ABSTRACT

A process for preparing cyclopentanone, at least comprising the following steps (i) to (iii):
(i) providing a mixture G(i) comprising cyclopentene;
(ii) providing liquid or supercritical N$_2$O or a liquid or supercritical gas mixture G(ii) comprising at least 20% by volume of N$_2$O, based on the total volume of the mixture G(ii);
(iii) contacting the mixture G(i) with the liquid or supercritical N$_2$O or the liquid or supercritical mixture G(ii) to obtain a mixture G(iii) comprising cyclopentanone,
wherein the mixture G(i) contains at least 25% by weight and at most 95% by weight, of cyclopentene, based on the total weight of the mixture G(i).

16 Claims, No Drawings

METHOD FOR THE PRODUCTION OF CYCLOPENTANONE

RELATED APPLICATIONS

This application is a national stage application (under 35 U.S.C. 371) of PCT/EP2005/010346 filed Sep. 23, 2005, which claims the benefit of German application 10 2004 046 171.6 filed Sep. 23, 2004.

The present invention relates to a process for preparing cyclopentanone, starting from a mixture which contains at most 95% by weight of cyclopentene. In addition to cyclopentene, the mixture may contain further solvents, and preference is given to further hydrocarbons, for example, as mixture constituents. According to the invention, cyclopentanone is obtained by reacting with $N_2O$, using either pure $N_2O$ or a gas mixture which comprises $N_2O$ in liquid or supercritical form. The present invention further relates to the use of specific mixtures obtained on the industrial scale and comprising cyclopentene, for example preferably hydrocarbon mixtures, for preparing cyclopentanone, using in particular a gas mixture which is also obtained on the industrial scale and comprises $N_2O$ for the reaction.

Currently, cyclopentanone is prepared on the industrial scale substantially exclusively by catalytically cyclizing adipic acid at high temperature. Although this reaction affords a good yield of cyclopentanone, about 42% of the adipic acid used is lost in the form of carbon dioxide and water. Among other disadvantages, this low atom efficiency reduces the economic viability of the process. Although the preparation starting from adipic ester is also possible, the atom efficiency in this case is even lower.

As an alternative on the laboratory scale, the literature offers the oxidation of cyclopentene with $N_2O$. For instance, GB 649,680 discloses the reaction of alkenes, for example cyclohexene or cyclopentene, with $N_2O$. However, the examples of this document do not explicitly disclose the reaction of cyclopentene with $N_2O$. Other unsubstituted olefins which are reacted with $N_2O$ in the examples are used either as pure compounds or together with the solvent dimethylaniline.

U.S. Pat. No. 2,636,898, which is equivalent to GB 649,680, equally does not disclose the reaction of cyclopentene with $N_2O$ in the examples. In these examples too, the unsubstituted olefins are reacted with $N_2O$ exclusively in pure form without the addition of a solvent.

In J. Chem. Soc., p. 2999-3008 (1951), F. S. Bridson-Jones et al. describe the reaction of olefins with $N_2O$, converting, for example, cyclohexene to cyclohexanone. In this case too, the cyclohexene is used as such, without addition, for example, of an additional solvent. Likewise described are, for example, the conversion of ethylene, acenaphthylene and methylenecyclobutane, using either cyclohexane or decalin as the solvent.

K. A. Dubkov et al., React. Kinet. Catal. Lett., Vol. 77, No. 1, p. 197-205 (2002) also describe the reaction of pure 99% cyclopentene with pure, medical grade $N_2O$. As in all other documents cited, no solvent is used in the reaction. Likewise, no further hydrocarbon in addition to cyclopentene is present in the reaction.

The more recent scientific articles of G. L. Panov et al, "Non-Catalytic Liquid Phase Oxidation of Alkenes with Nitrous Oxide. 1. Oxidation of Cyclohexene to Cyclohexanone", React. Kinet. Catal. Lett. Vol. 76, No. 2 (2002), p. 401-405, and K. A. Dubkov et al, "Non-Catalytic Liquid Phase Oxidation of Alkenes with Nitrous Oxide. 2. Oxidation of Cyclopentene to Cyclopentanone", React. Kinet. Catal. Lett. Vol 77, No. 1 (2002), p. 197-205 likewise describe oxidations of olefinic compounds with dinitrogen monoxide.

A scientific article "Liquid Phase Oxidation of Alkenes with Nitrous Oxide to Carbonyl Compounds" by E. V. Starokon et al. in Adv. Synth. Catal. 2004, 346, 268-274 also includes a mechanistic study of the oxidation of alkenes with dinitrogen monoxide in the liquid phase.

The synthesis of carbonyl compounds from alkenes with dinitrogen monoxide is also described in various international patent applications. For instance, WO 03/078370 discloses a process for preparing carbonyl compounds from aliphatic alkenes with dinitrogen monoxide. The reaction is carried out at temperatures in the range of from 20 to 350° C. and pressures of from 0.01 to 100 atm. WO 03/078374 discloses a corresponding process for preparing cyclohexanone. According to WO 03/078372, cyclic ketones having from 4 to 5 carbon atoms are prepared. According to WO03/078375, cyclic ketones are prepared under these process conditions from cyclic alkenes having from 7 to 20 carbon atoms. WO 03/078371 discloses a process for preparing substituted ketones from substituted alkenes. WO 04/000777 discloses a process for reacting di- and polyalkenes with dinitrogen monoxide to give the corresponding carbonyl compounds. There is no mention in these documents of the purification of dinitrogen monoxide.

The use of pure reactants as described in the above-cited scientific studies, may be of great value for the elucidation of reaction mechanisms, but is in practice associated with some disadvantages. For example, cyclopentene can only be obtained in the above-described high purity with very high technical complexity. In industrial processes in which cyclopentene is obtained in the required industrial scale amounts, it is present in mixtures with other hydrocarbons, for example cyclopentane. As a result of the similar boiling points, the separation, for example by distillative methods, is associated with considerable cost and inconvenience.

It is an object of the present invention to provide a process which enables the use as a reactant in cyclopentanone preparation of cyclopentene which is present in a mixture which has at most 95% by weight of cyclopentene, as obtained, for example in industrial scale processes.

We have found that this object is achieved by a process for preparing cyclopentanone, at least comprising the following steps (i) to (iii):

(i) providing a mixture G(i) comprising cyclopentene;
(ii) providing liquid or supercritical $N_2O$ or a liquid or supercritical gas mixture G(ii) comprising at least 20% by volume of $N_2O$, based on the total volume of the mixture G(ii);
(iii) contacting the mixture G(i) with the liquid or supercritical $N_2O$ or with the liquid or supercritical mixture G(ii) to obtain a mixture G(iii) comprising cyclopentanone, wherein the mixture G(i) contains at least 25% by weight and at most 95% by weight, of cyclopentene, based on the total weight of the mixture G(i).

Preference is given to using liquid $NO_2$ or a liquefied mixture G(ii).

DE 103 19 489.4 discloses a process for preparing cyclopentanone using dinitrogen monoxide as an oxidizing agent. However, there is no mention there of the use of liquid or supercritical dinitrogen monoxide.

In principle, the mixture G(i), in addition to cyclopentene, may contain any further compound. Suitable compounds also include those which may likewise react with $N_2O$ in the contacting of (iii). Preference is given in this context to those compounds which can in principle react with $N_2O$ but are inert toward $N_2O$ under the reaction conditions selected in (iii). The term "inert" as used in the context of the present invention refers to compounds which either do not react with $N_2O$ under the reaction conditions selected in (iii), or react to such a limited extent compared to the reaction of cyclopentene with $N_2O$ that at most 15% by weight, preferably at most 10% by weight and more preferably at most 5% by weight, of their reaction product with $N_2O$ is present in the mixture resulting from (iii), based in each case on the total weight of the mixture resulting from (iii).

The present invention therefore also relates to a process, wherein, as described above, the mixture G(i), in addition to cyclopentene, comprises at least one compound which is inert toward $N_2O$ in the course of the contacting of (iii).

Useful inert compounds in the context of the present invention are alkanes, for example cyclopentane, hexane, octane, decane, dodecane or benzene, or alkylbenzenes, for example toluene, xylenes, ethylbenzene, or ethers, for example methyl tert-butyl ether, tetrahydrofuran, diethyl ether or esters, for example methyl acetate, ethyl acetate, methyl benzoate, or nitriles, for example acetonitrile, benzonitrile, or alcohols, for example butanol, 2-ethylhexanol, ethanol or phenols, for example phenol, cresols, or amines, for example aniline, triethylamine, N,N-dimethylaniline, or mixtures of two or more of the compounds mentioned or two or more compounds of the classes mentioned.

Very particular preference is given to those compounds which do not react with $N_2O$ under the reaction conditions selected in (iii).

In the context of an embodiment of the process according to the invention which is preferred in this regard, the reactant mixture G(i) used is a mixture which is obtained from dissociation and partial hydrogenation of dicyclopentadiene in the presence of a solvent and cyclopentene, and the solvent is selected from the abovementioned inert compounds. Preference is given in this context to using a 2:1 mixture of dicyclopentadiene and toluene for the partial hydrogenation. This process is described, for example, in JP 2000053597 A, which is fully incorporated in this connection by reference into the context of the present application. According to JP 200053597 A, cyclopentadiene is obtained by thermolysis of dicyclopentadiene in the presence of an aromatic hydrocarbon, preferably toluene, the conversion being 98%. The resulting gas is passed into a stainless steel reaction tube which is charged with palladium/alumina catalyst. The gas is condensed with a cooler at the outlet of the reaction tube.

In a further preferred embodiment of the process according to the invention, the mixture G(i) consists of at least 99% by weight, based on the total weight of the mixture G(i), of hydrocarbons. In addition to the hydrocarbons, the mixture G(i) may therefore also contain at most 1% by weight of at least one further compound, in which case, among other compounds, at most 1% by weight of at least one of the abovementioned inert preferred compounds other than hydrocarbons may be present. At most 1% by weight of other compounds may also be present under the proviso that they do not interfere in the conversion of cyclopentene of (iii).

The term "hydrocarbon mixture" as used in the context of the present invention refers to a mixture of compounds, of which each is an unsubstituted hydrocarbon and therefore consists only of carbon and hydrogen atoms. The hydrocarbon mixtures which are used in the context of the present invention contain at most 1% by weight, based on the total weight of the mixture G(i), of further compounds. Greater preference is given to the mixture containing at most 0.5% by weight, greater preference to at most 0.1% by weight, greater preference to at most 0.01% by weight and very particular preference to at most 0.001% by weight, of further compounds. Preference is given in particular to mixtures G(i) which contain no further compounds within the measurement accuracy of the particular analysis methods used.

In a preferred embodiment, the mixture G(i) is liquid or supercritical under the reaction conditions selected in (iii). Preference is given in this context, inter alia, to mixtures G(i) which are liquid at ambient temperature and ambient pressure. For instance, these include mixtures of which each compound present is liquid at ambient temperature, and ambient pressure. Equally conceivable are mixtures which are liquid at ambient temperature and ambient pressure and contain at least one compound which is, for example, solid or gaseous at ambient temperature and ambient pressure, but is dissolved in the mixture G(i) at ambient temperature and ambient pressure.

In an embodiment of the process according to the invention which is likewise preferred, a mixture G(i) is used which consists of at least 99% by weight of $C_5$ hydrocarbons and hydrocarbons having more than 5 carbon atoms. Accordingly, at least one further $C_5$ hydrocarbon or at least one hydrocarbon having more than 5 carbon atoms or a mixture of at least one further $C_5$ hydrocarbon and at least one hydrocarbon having more than 5 hydrocarbon atoms may be present in addition to cyclopentene in G(i).

Accordingly, the present invention also describes a process as described above, wherein the mixture G(i) contains at least 99% by weight of $C_5$ hydrocarbons and hydrocarbons having more than 5 carbon atoms.

The hydrocarbons having more than 5 carbon atoms used which, among other hydrocarbons, are particularly preferred are the corresponding hydrocarbons already mentioned above in the context of the inert compounds.

As already mentioned above, the reactant mixtures G(i) used are preferably those mixtures as obtained in industrial scale processes. In the context of the present invention, preference is given in this context to mixtures which consist of at least 95% by weight, more preferably at least 97% by weight and particularly preferably of at least 99% by weight, of $C_5$, $C_6$ and $C_7$ hydrocarbons.

The present invention therefore relates to a process as described above, wherein the mixture G(i) contains at least 99% by weight of $C_5$ and $C_6$ or $C_5$ and $C_7$ or $C_5$ and $C_6$ and $C_7$ hydrocarbons.

In the context of the present invention, the mixture G(i), in addition to cyclopentene, may contain either at least one further $C_5$ hydrocarbon or at least one $C_6$ hydrocarbon or at least one $C_7$ hydrocarbon or a mixture of at least one further $C_5$ hydrocarbon and at least one $C_6$ hydrocarbon or a mixture of at least one further $C_5$ hydrocarbon and at least one $C_7$ hydrocarbon or a mixture of at least one further $C_5$ hydrocarbon and at least one $C_6$ hydrocarbon and at least one $C_7$ hydrocarbon.

In a preferred embodiment of the process according to the invention, the reactant mixture G(i) used is a hydrocarbon mixture which is obtained from a steam cracker or a refinery and contains cyclopentene. In this context, preference is given, for example, to $C_5$ cuts from steam crackers which contain substantially only $C_5$ and $C_6$ hydrocarbons. Hydrocarbons having more than 6 carbon atoms are not present in the $C_5$ cuts obtained on the industrial scale which, in addition to cyclopentene, comprise, for example, 2-butene, isopentane, 1-pentene, 2-methylbutene-1, trans-2-pentene, n-pentane, cis-2-pentene, 2-methylbutene-2, cyclopentane, 2,2-dimethylbutane, 2-methylpentane, 3-methylpentane, n-hexane and benzene. In general, a $C_5$ cut from a steam cracker contains cyclopentene in the range from 5 to 60% by weight and preferably in the range from 15 to 50% by weight.

The present invention therefore also describes a process as described above, wherein the mixture G(i) contains at least 99% by weight of a mixture of $C_5$ and $C_6$ hydrocarbons.

According to the invention, this mixture of substantially $C_5$ and $C_6$ hydrocarbons which is preferably obtained as a $C_5$ cut from a steam cracker may be used as such. Preference is given to subjecting the mixture of substantially $C_5$ and $C_6$ hydrocarbons before the reaction according to the invention of step (iii) to a purification in which lower-boiling compounds compared to cyclopentene are preferably again removed. While all conceivable methods can be used in this context, preference is given to distillatively separating the mixture.

In the context of the present invention, preference is given in this connection to obtaining mixtures G(i) which contain at most 10% by weight of $C_5$ and/or $C_6$ hydrocarbons which have a lower boiling point than cyclopentene. Should at least one $C_4$ hydrocarbon in some cases additionally be present in the mixture G(i) to be purified, preference is given to obtaining mixtures G(i) by the distillation used with preference which consist of at most 10% by weight of $C_4$ and/or $C_5$ and/or $C_6$ hydrocarbons which have a lower boiling point than cyclopentene. In the context of the present invention, particular preference is given in this connection to obtaining mixtures G(i) which contain at most 5% by weight, more preferably at most 3% by weight and particularly preferably at most 2% by weight, of $C_5$ and/or $C_6$ hydrocarbons which have a lower boiling point than cyclopentene. Should at least one $C_4$ hydrocarbon in some cases additionally be present in the mixture G(i) to be purified, preference is given to obtaining mixtures G(i) by the distillation used with preference which contain at most 5% by weight, more preferably at most 3% by weight and particularly preferably at most 2% by weight of $C_4$ and/or $C_5$ and/or $C_6$ hydrocarbons which have a lower boiling point than cyclopentene.

The present invention therefore also describes a process as described above, wherein the mixture G(i) consists of least 99% by weight, based on the total weight of the mixture G(i), of $C_5$ and $C_6$ hydrocarbons, and at most 2% by weight, based on the total weight of the mixture G(i), of hydrocarbons which are lower-boiling compared to cyclopentene.

In an embodiment of the process according to the invention which is likewise preferred, a mixture G(i) is used which consists of at least 99% by weight of $C_5$ and $C_7$ hydrocarbons. Accordingly, at least one further $C_5$ hydrocarbon or at least one $C_7$ hydrocarbon or a mixture of at least one further $C_5$ hydrocarbon and at least one $C_7$ hydrocarbon may be present in addition to cyclopentene in G(i).

Accordingly, the present invention also describes a process as described above, wherein the mixture G(i) contains at least 99% by weight of $C_5$ and $C_7$ hydrocarbons.

An example of a particularly preferred $C_7$ hydrocarbon is toluene.

In the context of an embodiment of the process according to the invention which is preferred in this regard, the reactant mixture G(i) used is a hydrocarbon mixture which is obtained from dissociation and partial hydrogenation of dicyclopentadiene in the presence of toluene as a solvent and contains cyclopentene. Preference is given in this context to partially hydrogenating a 2:1 mixture of dicyclopentadiene and toluene. This process is described, for example, in JP 2000053597 A, which is fully incorporated in this regard by reference into the context of the present application.

The mixtures obtained in this way generally contain cyclopentene in the range from 25 to 75% by weight, preferably in the range from 35 to 65% by weight and more preferably in the range from 40 to 60% by weight. In addition to cyclopentene, the reaction mixtures contain mainly cyclopentane and toluene. In general, the mixture which is obtained from dissociation and partial hydrogenation of a mixture of dicyclopentadiene and toluene and may be used as the mixture G(i) in the context of the process according to the invention consists of at least 99% by weight of cyclopentene, toluene and cyclopentane.

The mixture which is obtained in this preferred embodiment and consists of at least 99% by weight of cyclopentene, toluene and cyclopentane may be used as such.

In a further preferred embodiment, the mixture obtained from the dissociation and partial hydrogenation of a mixture of dicyclopentadiene and toluene is subjected before use as the mixture G(i) in the process according to the invention to at least one distillative separation in which a low boiler mixture is obtained which contains cyclopentene generally in the range from 60 to 95% by weight, preferably in the range from 70 to 90% by weight and more preferably in the range from 75 to 85% by weight. This low boiler mixture further contains toluene generally in the region of at most 20% by weight, preferably of at most 10% by weight and more preferably of at most 5% by weight, and cyclopentane generally in the range from 5 to 25% by weight, preferably in the range from 7 to 22% by weight and more preferably in the range from 10 to 20% by weight. This low boiler mixture is then used in the process according to the invention as mixture G(i).

Preference is further given to the mixture G(i) used in the process according to the invention containing cyclopentene in the range from 30 to 90% by weight, more preferably in the range from 40 to 90% by weight, even more preferably in the range from 45 to 90% by weight and especially preferably in the range from 50 to 85% by weight, based in each case on the total weight of the mixture G(i).

In particular, the present invention therefore also relates to the use of a cyclopentenic hydrocarbon mixture as a reactant for preparing cyclopentanone, wherein the cyclopentenic hydrocarbon mixture is either the $C_5$ cut of a steam cracker or the mixture obtained from the partial hydrogenation of cyclopentadiene and comprising cyclopentene or a mixture of the $C_5$ cut of a steam cracker and the mixture obtained from the partial hydrogenation of cyclopentadiene and comprising cyclopentene.

According to the invention, a gas mixture G(ii) which contains at least 20% by volume of $N_2O$ is used for the reaction of step (iii), and it is generally also possible to use pure $N_2O$, in which case the gas mixture G(ii) or the $N_2O$ is used in liquid or supercritical form, preferably in liquid form. Preference is given to selecting pressure and temperature in such a way that the gas mixture is present in liquid or supercritical form, more preferably in liquid form. It is also possible in accordance with the invention that the gas mixture G(ii) or the $N_2O$ is absorbed in a solvent.

The term "gas mixture" as used in the context of the present invention refers to a mixture of two or more compounds which are in the gaseous state at ambient pressure and ambient temperature. When the temperature is altered or the pressure is altered, the gas mixture may also be present in another state of matter, for example liquid, and is referred to subsequently in the context of the present invention as gas mixture.

According to the invention, this gas mixture is liquefied and then used in liquid form. Dinitrogen monoxide or the gas mixture comprising dinitrogen monoxide may be liquefied by all processes known to those skilled in the art, in particular by suitable selection of the pressure and of the temperature.

In a preferred embodiment, a gas mixture G(ii) is used which contains at least 20% by volume of $N_2O$, and preference is given in turn to mixtures G(ii) having an $N_2O$ content in the range from 20 to 97% by volume, more preferably in the range from 30 to 95% by volume, more preferably in the range from 40 to 94% by volume and especially preferably in the range from 50 to 93% by volume.

In the context of the present invention, the composition of the gas mixtures or of the liquefied gas mixtures is specified in % by volume. The data relate to the composition of the gas mixtures at ambient pressure and ambient temperature.

The present invention therefore also relates to a process as described above, wherein the mixture G(ii) contains at most 93% by volume of $N_2O$.

When a gas mixture G(ii) is used, it may also contain, in addition to $N_2O$, at least one further gas. Essentially all gases are conceivable in this context, as long as it is guaranteed that the reaction of cyclopentene with $N_2O$ of step (iii) is possible.

Preference is accordingly given to mixtures G(ii) which, in addition to $N_2O$, contain at least one inert gas. The term "inert gas" as used in the context of the present invention refers to a gas which, with regard to the reaction of $N_2O$ with cyclopentene, behaves inertly. Inert gases include, for example, nitrogen, carbon dioxide, carbon monoxide, argon, methane, ethane and propane.

Likewise present in the mixture G(ii) may also be gases which do not behave as inert gases in the reaction of $N_2O$ with cyclopentene. Such gases include, inter alia, $NO_x$ or, for example, oxygen. The term "$NO_x$" as understood in the context of the present invention refers to all $N_aO_b$ compounds where a is 1 or 2 and b is from 1 to 6, apart from $N_2O$. Instead of the term "$NO_x$", the term "nitrogen oxides" is also used in the context of the present invention. In such a case, preference is given to using those mixtures G(ii) whose content of these gases is at most 0.5% by volume, based on the total weight of the mixture G(ii).

The present invention therefore also relates to a process as described above, wherein the mixture G(ii) contains at most 0.5% by volume of oxygen or at most 0.5% by volume of nitrogen oxides or at most both 0.5% by volume of oxygen and 0.5% by volume of nitrogen oxides, based in each case on the total volume of the mixture G(ii). A value of, for example, 0.5% by volume refers in this context to a total content of all possible nitrogen oxides apart from $N_2O$ of 0.5% by volume.

In principle, the composition of the mixtures may be determined in the context of the present invention in any way known to those skilled in the art. In the context of the present invention, the composition of the gas mixtures G(ii) is determined by gas chromatography. However, it may also be determined by means of UV spectroscopy, IR spectroscopy or by wet-chemical methods.

According to the invention, the gas mixture G(ii) is used in liquid or supercritical form, preferably in liquid form. It is possible in accordance with the invention that the gas mixture (ii) is subjected before liquefaction to a treatment in order to reduce the concentration of inert and troublesome compounds in the gas mixture G(ii).

According to the invention this treatment may include, for example, an absorption of the gas mixture in a suitable solvent and subsequent desorption in order to remove inert compounds from the gas mixture. A suitable solvent is, for example, water, as described in DE 20 40 219.

According to the invention, the treatment of the gas mixture may also include a purification step to remove $NO_x$ from the gas mixture. Such processes for the removal of $NO_x$ are known in principle from the prior art. According to the invention, all processes known to those skilled in the art may be used for the removal of $NO_x$.

In particular, it is possible in the context of the present invention to use gas mixtures G(ii) which are obtained from industrial scale processes. Accordingly, should these mixtures G(ii) contain more than 0.5% by volume of oxygen and/or nitrogen oxides, they can generally be used in the process according to the invention. Preference is given to subjecting these mixtures G(ii), like such mixtures G(ii) of similar composition which are not obtained from industrial scale processes, before use in the process according to the invention, to at least one purification step in which the content of oxygen and/or nitrogen oxides is set to at most 0.5% by volume.

In a preferred embodiment of the present invention, the gas mixture G(ii) used is at least one $N_2O$-containing offgas of a chemical process.

In a preferred embodiment of the present invention, the dinitrogen monoxide source is at least one dinitrogen monoxide-containing offgas of a chemical process. The scope of the present invention also includes embodiments in which at least two nitrogen monoxide-containing offgases of a single plant serve as the dinitrogen monoxide source. Likewise included are embodiments in which at least one dinitrogen monoxide-containing offgas of one plant and at least one further dinitrogen monoxide-containing offgas of at least one further plant serve as the dinitrogen monoxide source.

Accordingly, the present invention also relates to a process as described above, wherein the dinitrogen monoxide source used is at least one dinitrogen monoxide-containing offgas of at least one industrial process.

It is equally possible in the context of the process according to the invention to selectively prepare dinitrogen monoxide for use in the process. Preference is given inter alia to the preparation via the thermal decomposition of $NH_4NO_3$, as described, for example, in U.S. Pat. No. 3,656,899, whose contents on this subject are incorporated fully by reference into the context of the present application. Preference is likewise further given to the preparation via the catalytic oxidation of ammonia, as described, for example, in U.S. Pat. No. 5,849,257 or in WO 98/25698, whose contents on this subject are incorporated fully by reference into the context of the present application.

In the context of the present invention, the term "dinitrogen monoxide source" relates both to embodiments in which the offgas mentioned is used in unmodified form in the inventive reaction of cyclopentene and embodiments in which at least one of the offgases mentioned is subjected to a modification.

The term "modification" as used in this context within the scope of the present invention refers to any suitable process by which the chemical composition of an offgas is altered. Accordingly, the term "modification" embraces inter alia embodiments in which a dinitrogen monoxide-containing offgas is concentrated with regard to the dinitrogen monoxide content in at least one suitable process. Such processes are described, for example, in DE-A 27 32 267, EP 1 076 217 A2 or WO 00/73202 A1, whose contents on this subject are incorporated fully by reference into the context of the present application.

According to the invention, preference is given to subjecting the offgas to a treatment comprising an absorption in a suitable solvent and subsequent desorption in order to remove inert compounds. A suitable solvent is, for example, water, as described in DT 20 40 219.

In one example of a preferred embodiment of the process according to the invention, it is possible to concentrate by feeding the abovementioned dinitrogen monoxide-containing offgas to at least one adsorption column and to dissolve the dinitrogen monoxide in at least one organic solvent. An example of a solvent suitable for this purpose is cyclopentene.

This inventive process variant offers the advantage that the resulting solution of dinitrogen monoxide in cyclopentene can be fed to the inventive reaction without further workup. This solution of dinitrogen monoxide in cyclopentene may contain dinitrogen monoxide in all conceivable concentrations up to saturation. In other embodiments, at least one further solvent or a mixture of cyclopentene and at least one further solvent may be used for the adsorption. Such further solvents are, for example, all suitable common organic solvents. Preferred solvents include N-methylpyrrolidone, dimethylformamide, dimethyl sulfoxide, propylene carbonate, sulfolane or N,N-dimethylacetamide. When at least one further solvent or a mixture of cyclopentene and at least one further solvent is used, in a further preferred embodiment, the dinitrogen monoxide is obtained at least partly, preferably substantially fully, from the dinitrogen monoxide-enriched solution in at least one suitable desorption step, and fed to the inventive reaction.

In a further embodiment, the chemical composition of an offgas may also be altered by adding pure dinitrogen monoxide to the offgas.

In a further preferred embodiment of the present invention, the at least one dinitrogen monoxide-containing offgas stems from an adipic acid plant, a dodecanedioic acid plant, a hydroxylamine plant and/or a nitric acid plant, and the latter is preferably operated in turn with at least one offgas of an adipic acid plant, a dodecanedioic acid plant or a hydroxylamine plant.

In a very particularly preferred embodiment, the gas mixture G(ii) used is the offgas stream of an adipic acid plant in which generally from 0.8 to 1.0 mol of $N_2O$ is formed by oxidizing cyclohexanol/cyclohexanone mixtures with nitric acid per mole of adipic acid formed. However, as described, for example, in A. Uriate et al., Stud. Surf. Sci. Catal. 130, p. 743-748 (2000), the offgases of adipic acid plants also contain, in different concentrations, further constituents including nitrogen, oxygen, carbon dioxide, carbon monoxide, nitrogen oxides, water and volatile organic compounds.

As already described above, such an offgas stream of an adipic acid plant may be used directly in the process according to the invention. Preference is given to purifying the offgas stream. Conceivable for this purpose are, for example, all processes which enable the oxygen and/or nitrogen oxides content of the offgas stream each to be set to at most 0.5% by volume. The above-cited document of A. Uriate et al. discloses various means of purifying such an offgas stream for use in catalytic benzene hydroxylation. Absorption processes are described, for example pressure swing absorption, membrane separation processes, low temperature distillation or a combination of selective catalytic reduction with ammonia, followed by catalytic removal of oxygen. All of these purification methods can be employed to purify the offgas stream of an adipic acid plant which is used in the process according to the invention.

Particular preference is given in the context of the present invention to purifying the offgas stream of an adipic acid plant in the case that it contains in each case more than 0.5% by volume of oxygen and/or nitrogen oxides. Preference is given to effecting this purification by distillation.

In a likewise preferred embodiment, the gas mixture G(ii) used is the offgas steam of a dodecanedioic acid plant. Compared with the adipic acid plant, this dodecanedioic acid plant is substantially of an identical plant type.

An example of a typical composition of an offgas of a dodecanedioic acid plant or of an adipic acid plant is reproduced in the following table:

| Component | Concentrations/% by wt. |
|---|---|
| $NO_x$ | 19-25 |
| $N_2O$ | 20-28 |
| $N_2$ | 30-40 |
| $O_2$ | 7-10 |
| $CO_2$ | 2-3 |
| $H_2O$ | ~7 |

The offgas stream of a dodecanedioic acid plant may be used directly in the process according to the invention. Preference is given to purifying the offgas stream of the dodecanedioic acid plant before use in the process according to the invention. In this case, for example, the content of oxygen and/or nitrogen oxides in the offgas stream is advantageously adjusted to contents in the region of in each case at most 0.5% by volume, i.e. from 0 to 0.5% by volume. The above-cited document of A. K. Uriarte et al discloses various means of purifying such an offgas stream for use in catalytic benzene hydroxylation. Absorption processes are described, for example pressure swing absorption, membrane separation processes, low temperature distillation or a combination of selective catalyst reduction with ammonia, followed by catalytic removal of oxygen. All of these purification methods can also be employed to purify the dinitrogen monoxide-containing offgas stream of an industrial plant, for example of a dodecanedioic acid plant or of an adipic acid plant or of a nitric acid plant. Very particular preference is given to the distillative purification and thus the distillative concentration of the offgas stream of a dodecanedioic acid plant or of an adipic acid plant or of a nitric acid plant.

Particular preference is given in the context of the present invention to purifying the offgas stream of a dodecanedioic acid plant in the case that it contains in each case more than 0.5% by volume of oxygen and/or nitrogen oxide.

In a likewise preferred embodiment, the gas mixture G(ii) used is the offgas stream of a nitric acid plant which is fed partly or fully with offgases, comprising dinitrogen monoxide and nitrogen oxides, from other processes. In such nitric acid plants, nitrogen oxides are adsorbed and for the most part converted to nitric acid, while dinitrogen monoxide is not converted. For example, such a nitric acid plant may be fed by nitrogen oxides which are prepared by selective combustion of ammonia, and by offgases of an adipic acid plant and/or by offgases of a dodecanedioic acid plant. It is equally possible to feed such a nitric acid plant solely by offgases of an adipic acid plant and/or by offgases of a dodecanedioic acid plant.

In principle, the offgases of such nitric acid plants also contain different concentrations of further constituents including nitrogen, oxygen, carbon dioxide, carbon monoxide, nitrogen oxides, water and volatile organic compounds.

An example of a typical composition of an offgas of such a nitric acid plant is reproduced in the following table:

| Component | Concentrations/% by wt. |
|---|---|
| $NO_x$ | <0.1 |
| $N_2O$ | 8-36 |
| $N_2$ | 57-86 |
| $O_2$ | 3-9 |

-continued

| Component | Concentrations/% by wt. |
|---|---|
| $CO_2$ | 1-4 |
| $H_2O$ | ~0.6 |

The offgas stream of a nitric acid plant may be used directly in the process according to the invention. Preference is given to purifying the offgas stream of the nitric acid plant before use in the process according to the invention. For example, the content of oxygen and/or nitrogen oxides in the offgas stream are advantageously adjusted to contents in the region of at most 0.5% by volume, i.e. of in each case from 0 to 0.5% by volume. Suitable processes by which these values can be adjusted are described above in the context of the adipic acid plant and dodecanedioic acid plant. In the context of the offgases of the nitric acid plant, very particular preference is also given to distillative purification and thus distillative concentration.

In the context of the present invention, particular preference is given to purifying the offgas stream of a nitric acid plant in the case that it contains in each case more than 0.5% by volume of oxygen and/or nitrogen oxides.

In a likewise preferred embodiment of the process according to the invention, the gas mixture G(ii) used is the offgas stream of a hydroxylamine plant, in which, for example, ammonia is initially oxidized with air or oxygen to give NO, in the course of which small amounts of dinitrogen monoxide are formed as a by-product. The NO is subsequently hydrogenated with hydrogen to give hydroxylamine. Since dinitrogen monoxide is inert under the hydrogenation conditions, it accumulates in the hydrogen circuit. In preferred process versions, the purged stream of a hydroxylamine plant contains dinitrogen monoxide in the range of from 9 to 13% by volume in hydrogen. Preference is given to suitably concentrating this stream with regard to the dinitrogen monoxide content before use in the process according to the invention.

Accordingly, the present invention also describes a process as described above, wherein the gas mixture G(ii) used is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant.

Accordingly, the present invention also describes the use of a cyclopentenic hydrocarbon mixture as a reactant for preparing cyclopentanone, wherein the cyclopentenic hydrocarbon mixture is either the $C_5$ cut of a steam cracker or the mixture obtained from the partial hydrogenation of cyclopentadiene and comprising cyclopentene or a mixture of the $C_5$ cut of a steam cracker and the mixture obtained from the partial hydrogenation of cyclopentadiene and comprising cyclopentene, and wherein the offgas stream of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant is used for the reaction.

The present invention likewise describes the use as described above, wherein the content of the offgas stream of the adipic acid plant and/or of the dodecanedioic acid plant and/or of the hydroxylamine plant and/or of the nitric acid plant operated with the offgas of an adipic acid plant and/or of a dodecanedioic acid plant and/or of a hydroxylamine plant of oxygen and/or nitrogen oxides has been set before the reaction with the hydrocarbon mixture to in each case at most 0.5% by volume, based on the total volume of the offgas stream.

The reaction of step (iii) may generally be effected by all process procedures in which cyclopentanone is formed from the mixture G(i) and the mixture G(ii). In particular, continuous process procedures and methods of the reaction as a batch reaction are possible.

In a preferred embodiment, the conversion of step (iii) is effected in batch mode. Preference is given in this context in turn to initially charging the mixture G(i) in a suitable reaction vessel. Since the reaction, as described below, is preferably effected at pressures higher than atmospheric pressure, the reaction vessel used is preferably an autoclave.

The mixture G(i) is generally initially charged at temperatures in the range from 0 to 320° C., preferably in the range from 180 to 300° C. and more preferably in the range from 200 to 290° C. The pressures are generally in the range from 1 to 500 bar, preferably in the range from 10 to 365 bar and more preferably in the range from 25 to 250 bar.

Once the mixture G(i) has been initially charged under the above-specified temperatures and pressures, it is contacted with the mixture G(ii), and the air present in the reaction vessel may be at partly removed before the contacting by a suitable measure. Preference is given to purging the reaction vessel with at least one gas or gas mixture, and purging may be effected using, for example, nitrogen or another suitable inert gas or a mixture of two or more of these gases. Particular preference is given to using nitrogen as the purging gas.

The mixture G(i) and the mixture G(ii) or the pure $N_2O$ are introduced in amounts in which the molar ratio of cyclopentene to $N_2O$ is generally in the range from 0.05 to 5, preferably in the range from 0.5 to 3 and more preferably in the range from 0.9 to 1.5.

To contact the mixtures G(i) and G(ii), the mixture G(ii) is generally introduced into the reaction vessel at a pressure in the range from 5 to 500 bar, preferably in the range from 10 to 365 bar and more preferably in the range from 25 to 250 bar. The temperatures at which the contacting is effected are adjusted by suitable measures in such a way that the reaction of the cyclopentene present in the mixture G(i) with the $N_2O$ present in the mixture G(ii) preferably takes place in the liquid or supercritical phase. Accordingly, the temperatures at which the reaction takes place are generally in the range from 150 to 320° C., preferably in the range from 180 to 300° C. and more preferably in the range from 200 to 290° C.

In a particularly preferred embodiment of the process according to the invention, the mixture G(ii) is initially introduced into the reaction vessel at the above-specified pressures and the temperature in the reaction vessel is subsequently increased at a rate of generally from 1 to 10° C./min, preferably from 1.5 to 5° C./min and more preferably from 2 to 4° C./min.

When the temperature is increased to such an extent that the above-specified temperature required for the reaction is achieved, this temperature is generally maintained for a period in the range from 1 to 48 h, preferably in the range from 2 to 30 h and more preferably in the range from 5 to 25 h. It is conceivable not to keep the temperature constant, but rather to vary it in a suitable manner within the above-specified limits.

The present invention therefore also relates to a process as described above, wherein step (iii) comprises at least the following stages (a) to (d):

(a) introducing the mixture G(i) into a reaction vessel at a temperature in the range from 0 to 320° C. and a pressure in the range from 1 to 500 bar;

(b) contacting the mixture G(i) in the reaction vessel with the mixture G(ii) at a pressure in the range from 5 to 500 bar;
(c) increasing the temperature of the mixture obtained in (b) at a rate in the range from 1 to 10° C./min. to a temperature in the range from 150 to 320° C.;
(d) holding the temperature set in (c) for a period in the range from 0.1 to 48 h.

On completion of the reaction of the cyclopentene with $N_2O$, the mixture under pressure in the reaction vessel is cooled. The interior of the reaction vessel is decompressed, during or after the cooling, or both during and after the cooling.

In addition to the above-described reaction in a batch reactor, the process according to the invention may in principle be carried out in any other reactor suitable for this purpose. It is likewise possible to combine two or more identical or different reactors. An example of one possible apparatus for the reaction of (iii) is at least one bubble column. Preference is given to carrying out the reaction of (iii) in at least one continuous reactor. For example, the reaction of (iii) may be effected in a CSTR (continuous stirred tank reactor) or in a CSTR battery. Preference is further given to at least one of the at least one continuous reactors being a continuous tubular reactor.

The present invention therefore also relates to a process as described above, wherein, in step (iii), the mixtures G(i) and G(ii) are contacted in a continuous reactor, in particular in a continuous tubular reactor.

In a further preferred embodiment, at least one of the continuous tubular reactors used in accordance with the invention is a tube bundle reactor.

The mixtures G(i) and G(ii) may be contacted in the continuous reactors substantially under any suitable reaction conditions which allow cyclopentene to react with $N_2O$ to give cyclopentanone and under which the mixture is in liquid or supercritical form. Preference is given in particular to selecting the reaction conditions in the at least one continuous reactor in such a way that the reaction of (iii) is effected in the liquid or supercritical phase. Preference is further given to reaction conditions in which the entire contents of the reactor are liquid. The term "reactor contents" refers to the mixtures G(i) and G(ii) after they have been introduced into the reactor, and also the mixture resulting from these mixtures. Preference is given in particular to introducing the mixtures G(i) and G(ii) separately into the reactor.

The present invention accordingly also relates to a process as described above, wherein the continuous reactor, in particular the continuous tubular reactor, is filled substantially exclusively with liquid during the reaction of (iii).

The present invention likewise relates to a process as described above, wherein the contents in the continuous reactor, in particular in the continuous tubular reactor, during the reaction in (iii) remain substantially in the supercritical phase.

Very particular preference is given to selecting the reaction conditions in such a way that the mixture in the reactor is homogeneous and monophasic.

The mixture G(i) is generally introduced into the continuous reactor at temperatures in the range from 0 to 320° C., preferably in the range from 180 to 300° C. and more preferably in the range from 200 to 290° C., and the pressures are generally in the range from 1 to 500 bar, preferably in the range from 10 to 365 bar and more preferably in the range from 25 to 300 bar.

The mixture G(ii) is generally introduced into the continuous reactor at temperatures in the range from 0 to 320° C., preferably in the range from 180 to 300° C. and more preferably in the range from 200 to 290° C., and the pressures are generally in the range from 5 to 500 bar, preferably in the range from 10 to 365 bar and more preferably in the range from 25 to 300 bar.

In the continuous reactor, the mixtures G(i) and G(ii) are contacted. The mixture G(i) and the mixture (ii), and the pure $N_2O$, are used in such ratios in which the molar ratio of cyclopentene to $N_2O$ is generally in the range from 0.05 to 10, preferably in the range from 0.5 to 7 and more preferably in the range from 1 to 5.

However, it is equally possible in the context of the present invention to mix the mixture G(ii) and the mixture G(i) or a portion of the mixture G(i) and to introduce this mixture into the reactor. According to the invention, the mixture G(ii) and the mixture G(i) or a portion of the mixture G(i) are mixed at temperatures at which no reaction takes place. Preference is given to effecting the mixing at a temperature in the range of from 80 to 200° C., preferably in the range of from 90 to 150° C., in particular in the range of from 100 to 120° C.

The reaction of the cyclopentene present in the mixture G(i) with the $N_2O$ present in the mixture G(ii) in the at least one continuous reactor is effected at temperatures of generally in the range from 150 to 320° C., preferably in the range from 180 to 300° C. and more preferably in the range from 200 to 290° C. The pressures in the continuous reactor are generally in the range from 5 to 500 bar, preferably in the range from 10 to 400 bar and more preferably in the range from 100 to 365 bar.

The residence time of the reaction mixture in the continuous reactor is generally in the range from 0.1 to 48 h, preferably in the range from 0.2 to 5 h and more preferably in the range from 0.3 to 2.5 h. It is conceivable not to keep the temperature or the pressure or both in the reactor constant, but rather to vary them in a suitable manner within the above-specified limits.

The present invention therefore also relates to a process as described above, wherein step (iii) comprises at least the following stages (aa) to (dd):

(aa) introducing the mixture G(i) into a continuous reactor at a temperature in the range from 0 to 320° C. and a pressure in the range from 1 to 500 bar;
(bb) introducing the mixture G(ii) into the continuous reactor at a temperature in the range from 0 to 320° C. and a pressure in the range from 5 to 500 bar;
(cc) contacting the mixture G(i) with the mixture G(ii) in the continuous reactor at a temperature in the range from 100 to 320° C. and a pressure in the range from 5 to 500 bar;
(dd) reacting the mixtures G(i) and G(ii) over a residence time of the reaction mixture in the continuous reactor in the range from 0.1 to 48 h.

As already detailed, it is also possible in the context of the present invention to mix the mixtures G(i) and G(ii) before introduction into the reactor. In an alternative embodiment, the present invention therefore also relates to a process as described above, wherein the step (iii) comprises at least the following stages (aa') to (dd'):

(aa') mixing the mixture G(i) or a portion of the mixture G(i) with the mixture G(ii) at a temperature of from 80 to 200° C.;
(bb') introducing the mixture obtained in step (aa') and any further mixture G(i) into a continuous reactor at a temperature in the range of from 0 to 320° C. and a pressure in the range from 5 to 500 bar;

(cc') increasing the temperature of the mixture obtained in (bb') to a temperature in the range of from 100 to 320° C.;
(dd') holding the temperature set in (cc') for a period in the range of from 0.1 to 48 h.

The process according to the invention in accordance with the above-described process procedures, using the mixtures G(i) and G(ii) achieves cyclopentene conversions which are generally at least 10%, preferably at least 20%, in particular at least 30% and more preferably at least 50%. The upper limit of the conversions is generally 90%, in particular 98%, preferably 99% and more preferably 99.9%.

The cyclopentanone selectivities of the reaction with respect to cyclopentene are generally in the range from 92 to 99.5%.

The present invention therefore also describes a process as described above, wherein the cyclopentene used in the range from 10 to 99.9%, based on the total amount of cyclopentene used, is converted at a cyclopentanone selectivity with respect to cyclopentene in the range from 92 to 99.5%.

The mixture obtained in step (iii) and containing cyclopentanone can be further worked up by all suitable processes for obtaining cyclopentanone. Particular preference is given in this context to distillative processes.

The examples which follow illustrate the invention in more detail.

EXAMPLES

Example 1

Oxidation of Cyclopentene/cyclopentane to Cyclopentanone

From corresponding reservoirs, 2000 g/h of an approx. 1:1 cyclopentene/cyclopentane mixture (of which 400 g/h are fresh and 1600 g/h are recycled reactant, 1:1 cyclopentene/cyclopentane) and 140 g/h of a liquid mixture having 93.5% by weight of $N_2O$ are pumped via a static mixer into a tubular reactor (jacketed tube, coiled, internal diameter 6 mm, length 85 m). The tube is thermostatted to 280° C. by pumping heat carrier oil in circulation in the jacket. The internal reactor pressure is controlled at 300 bar. After passing through the reaction zone, the reaction mixture is decompressed in two flash vessels initially to 16 bar and subsequently to 5 bar in order to remove $N_2$ formed, unconverted $N_2O$ and inerts present in the $N_2O$ (mainly $N_2$ and $CO_2$).

The liquid product is then distilled in a column having at least 27 theoretical plates at 1 bar ($T_{bottom}$=79° C., $T_{top}$=46° C.). The top product obtained is on average 1600 g/h of unconverted cyclopentene in a mixture (approx. 1:1) with cyclopentane which is recycled back into the reactor. The bottom effluent which contains approx. 50% cyclopentanone (crude cyclopentanone) and approx. 50% cyclopentane is transferred into a product vat.

On average, 237 g/h of crude cyclopentanone are obtained which still have to be separated from cyclopentane in a further distillation. The selectivity for cyclopentanone is 96% (based on cyclopentene converted).

We claim:
1. A process for preparing cyclopentanone comprising the following steps (i) to (iii):
(i) providing a mixture G(i) comprising cyclopentene;
(ii) providing liquid or supercritical N2O or a liquid or supercritical gas mixture G(ii) comprising at least 20% by volume of N2O, based on the total volume of the mixture G(ii);
(iii) contacting the mixture G(i) with the liquid or supercritical N2O or with the liquid or supercritical mixture G(ii) to obtain a mixture G(iii) comprising cyclopentanone,
wherein the mixture G(i) contains at least 25% by weight and at most 95% by weight, of cyclopentene, based on the total weight of the mixture G(i),
wherein the gas mixture G(ii) used is at least one dinitrogen monoxide containing offgas of a chemical process, and said mixture G(ii) has an N2O content in a range from 20 to 97 percent by volume,
and wherein, in step (iii), the mixtures G(i) and G(ii) are contacted in a continuous reactor at temperatures in the range from 200 to 290° C. and pressures in the range from 10 to 400 bar, wherein the residence time of the reaction mixture in the continuous reactor is in a range from 0.3 to 2.5 hours.

2. The process as claimed in claim 1, wherein the mixture G(i), in addition to cyclopentene, comprises at least one compound which is inert toward N2O in the course of the contacting of (iii).

3. The process as claimed in claim 1, wherein the mixture G(i) contains at least 99% by weight, based on the total weight of the mixture, of hydrocarbons.

4. The process as claimed in claim 1, wherein the mixture G(i) contains at least 99% by weight of C5 and C6 or C5 and C7 or C5 and C6 and C7 hydrocarbons.

5. The process as claimed in claim 1, wherein the mixture G(ii) contains at most 93% by volume of N2O.

6. The process as claimed in claim 1, wherein the mixture G(ii) contains at most 0.5% by volume of oxygen or at most 0.5% by volume of nitrogen oxides or at most both 0.5% by volume of oxygen and 0.5% by volume of nitrogen oxides, based in each case on the total volume of the mixture G(ii).

7. The process as claimed in claim 1, wherein the continuous reactor is filled exclusively with liquid during the conversion of (iii).

8. The process as claimed in claim 1, wherein the reactor contents in the continuous reactor are in the supercritical phase during the reaction in (iii).

9. The process as claimed in claim 2, wherein the mixture G(i) contains at least 99% by weight of C5 and C6 or C5 and C7 or C5 and C6 and C7 hydrocarbons.

10. The process as claimed in claim 9, wherein the mixture G(ii) contains at most 93% by volume of N2O.

11. The process as claimed in claim 10, wherein the mixture G(ii) contains at most 0.5% by volume of oxygen or at most 0.5% by volume of nitrogen oxides or at most both 0.5% by volume of oxygen and 0.5% by volume of nitrogen oxides, based in each case on the total volume of the mixture G(ii).

12. The process as claimed in claim 1, wherein the at least one dinitrogen monoxide-containing offgas stems from an adipic acid plant, a dodecanedioic acid plant, a hydroxylamine plant and/or a nitric acid plant operated with the offgas of an adipic acid plant and/or of a dodecanedioic acid plant and/or of a hydroxylamine plant.

13. The process as claimed in claim 11, wherein the mixture G(i) contains at least 99% by weight of C5 and C6 hydrocarbons.

14. The process as claimed in claim 11, wherein the mixture G(i) contains at least 99% by weight of C5 and C7 hydrocarbons.

15. The process as claimed in claim 1, wherein the at least one dinitrogen monoxide-containing offgas stems from an adipic acid plant, a dodecanedioic acid plant, a hydroxylamine plant and/or a nitric acid plant operated with the offgas of an adipic acid plant and/or a nitric acid plant operated with the offgas of an adipic acid plant and/or of a dodecanedioic acid plant and/or of a hyrdroxylamine plant.

16. The process as claimed in claim 1, wherein G(i) comprises a hydrocarbon mixture comprises at least 25% by weight and at most 95% by weight, of cyclopentene, based on the total weight of the mixture G(i), and another hydrocarbon not cyclopentene.

* * * * *